United States Patent [19]
Melzer et al.

[11] Patent Number: 5,389,103
[45] Date of Patent: Feb. 14, 1995

[54] SURGICAL STITCHING APPARATUS

[75] Inventors: Andreas Melzer, Wiesbaden; Gerhard Buess, Bebenhausen; Rainer Trapp, Graben-Neudorf; Klaus-Peter Brhel, Philippsburg, all of Germany

[73] Assignee: Kernforschungszentrum Karlsruhe GmbH, Karlsruhe, Germany

[21] Appl. No.: 213,732

[22] Filed: Mar. 16, 1994

[30] Foreign Application Priority Data

Jul. 23, 1991 [DE] Germany .............................. 4124381
Jul. 23, 1991 [DE] Germany .............................. 4124383
Nov. 30, 1991 [DE] Germany .............................. 4139628

[51] Int. Cl.⁶ ............................................. A61B 17/04
[52] U.S. Cl. ................................... 606/144; 606/139; 606/147; 112/169; 112/171
[58] Field of Search ........................ 606/139, 144–148; 112/169, 171

[56]  References Cited
U.S. PATENT DOCUMENTS

| 1,037,864 | 9/1912 | Carlson et al. | 606/145 |
|---|---|---|---|
| 2,880,728 | 4/1959 | Righls . | |
| 3,090,385 | 5/1963 | Curtis | 606/146 |
| 3,692,224 | 9/1972 | Aslafiev . | |
| 3,946,740 | 3/1976 | Bassett | 606/145 |
| 4,236,470 | 12/1980 | Stenson . | |
| 4,836,205 | 6/1989 | Barrett . | |
| 4,935,027 | 6/1990 | Yoon . | |

FOREIGN PATENT DOCUMENTS

| 0174843 | 3/1986 | European Pat. Off. . | |
|---|---|---|---|
| 0315371 | 5/1989 | European Pat. Off. . | |
| 2447719 | 4/1976 | Germany . | |
| 1725847 | 4/1992 | U.S.S.R. | 606/148 |

*Primary Examiner*—Stephen C. Pellegrino
*Assistant Examiner*—Gary Jackson
*Attorney, Agent, or Firm*—Klaus J. Bach

[57]  ABSTRACT

In a surgical stitching apparatus for endoscopically performing sutures of tissue or vessels having a drive mechanism including concentric tubes with an operating handle structure at one end and a stitching head mounted at the distal end thereof, the stitching head includes a stationary and a movable mouthpiece each with clamping structures for engaging the tips of a needle each comprising movable and stationary halves with the movable half on the stationary mouthpiece being operatively connected to one of the concentric tubes and the movable mouthpiece being connected to another of the concentric tubes which is hand-operable by a movable handle on the operating handle structure, and the one concentric tube is operable by a pedal switch-controlled mechanism mounted on the operating handle structure for foot operation of the clamping structure on the stationary mouthpiece.

12 Claims, 5 Drawing Sheets

SURGICAL STITCHING APPARATUS

This application is a continuation-in-part application of international application No. PCT/DE92/00589 filed Jul. 21, 1992 and claiming priority of German pat. appl. Nos. P411438.1 of Jul. 23, 1991; P4124383.8 of Jul. 23, 1991 and P4139628.6 of Nov. 30, 1991.

BACKGROUND OF THE INVENTION

1. Field of the Invention

The invention relates to a surgical stitching apparatus by which a stitch may be made during surgery remotely and/or endoscopically.

It is the object and purpose of such instruments to limit, to a necessary minimum, the injury to a body to be operated on for a particular surgery and further to facilitate work of the surgeon during the surgical procedures. This technique is known as minimal invasive surgery (MIC).

2. Description of the Prior Art

From EP 0174843 A2 a sewing and stapling apparatus is known which can be inserted into the body of a patient via an instrument channel and which can be operated from without. The sewing head of the apparatus is open at the side thereof. This is where a suction pipe ends by means of which the tissue can be drawn in so that a tissue fold is formed. A needle with a thread extending through the needle ear then moves parallel to the apparatus axis and penetrates the tissue. The thread carried along can be held so as to form a loop by means of a catching device. A knot is formed separately.

U.S. Pat. No. 4,935,027 discloses a surgical instrument as well as a method of suturing from a remote location or endoscopically. The jaw members of the instrument are hollow and, in closed state, form an ear through which the suturing thread can be pushed or moved. The jaw ends are so formed that, in spite of being hollow, they can pierce the tissue to be sutured.

After each suturing step, or the whole suturing procedure, a knot is formed, for example, at the outside, and is then moved inwardly for knotting. This, in any case, requires additional instruments.

Acceptance of such suturing instruments by the surgeon is determined essentially by the degree of rapid acclimatization and by an as easy and conflict-free operability as possible.

It is the object of the present invention to provide a stitching apparatus which can be inserted and operated through an instrument channel and by which surgical sutures on tissue or vessels can be performed and knots can be formed to a large extent without additional instruments. This object is solved by the features characterized in claim 1.

SUMMARY OF THE INVENTION

In a surgical stitching apparatus for endoscopically performing sutures of tissue or vessels having a drive mechanism including concentric tubes with an operating handle structure at one end and a stitching head mounted at the distal end thereof, the stitching head includes a stationary and a movable mouthpiece each with clamping structures for engaging the tips of a needle each comprising movable and stationary halves with the movable half on the stationary mouthpiece being operatively connected to one of the concentric tubes and the movable mouthpiece being connected to another of the concentric tubes which is hand-operable by a movable handle on the operating handle structure, and the one concentric tube is operable by a pedal switch-controlled mechanism mounted on the operating handle structure for foot operation of the clamping structure on the stationary mouthpiece.

For grasping tissue, the stitching apparatus preferably has at its distal end a mouth area which consists of a stationary and a movable mouthpiece, which, because of its design features, can be utilized as a grasping instrument when the stitching needle is not mounted.

The free ends of both mouthpieces are provided with clamping structures adapted to receive a stitching needle in a form- and clearly defined force-locking manner. In the arrangement the stitching needle is engaged selectively at one end or both ends and it can be transferred from one clamping structure to the other.

Movement of the movable mouthpiece is achieved by the surgeon with one hand at the movable handle portion of the handle structure and consequently also the pulling of the needle from, and its insertion into, one clamping structure can be performed one-handedly. On the other hand, clamping the needle into the other clamping structure or its release therefrom is effected pneumatically by means of a pedal switch operated by the foot of the surgeon. For this purpose, a pressurized air pipe is connected to the pedal switch from which an air pipe leads to the connecting nozzle of a miniature air cylinder at the handle structure which, depending on the pressure within, abuts, via a shift lever mechanism and a drive tube extending through the instrument channel, one half of the clamping structure in a form- and clearly defined force-locking manner or moves it away from, the other.

The procedure of piercing through the tissue or a vessel part to be sutured and the needle transfer procedure are therefore clearly separated from one another. Consequently the surgeon's other hand is always free for possibly needed corrective guidance of the stitching apparatus at the point of operation.

The subclaims define an advantageous embodiment of the stitching apparatus and the operating handle structure.

Both clamping devices at the mouthpieces preferably have the negative shape of the needle ends which consist of tip, bulge portion and reduced diameter shank portion. The transition from the bulge portion to the reduced diameter shank portion is by way of a truncated cone or pyramid corresponding to the shape of the needle tip. Pulling the needle tip from, or inserting it into, the clamping structure at the movable mouthpiece therefore occurs without damaging it and with a predetermined force, that is, with a limited force. The same applies to the clamping of the needle point at the clamping structure of the stationary mouthpiece, since the pressure in the miniature air cylinder can be limited and since, by the design of the shift lever mechanism, the engagement force of the movable half with the stationary half of the clamping structure can be adjusted.

For knotting at the stitching location it is further advantageous if the movable portion of the operating handle structure can be position-locked by a releasable catch structure and can again be released by pulling beyond a particular pressure point.

Depending on the operation to be performed and the stitching procedure to be followed in connection therewith, it is also advantageous to have two differently designed embodiments of the mouth area available. One is characterized in that the mouth area of the stitching apparatus comprises two mouthpieces which are arranged equally normal to the axis of the stitching apparatus, wherein the movable mouthpiece is slidable by the operating handle axially toward and from the stationary mouthpiece so that a stitching needle mounted at one or both of its ends extends parallel to the apparatus axis. Suitably, the needle utilized in connection with this type of stitching apparatus is straight so that tissue or vessel parts can only be pierced by the needle but cannot be torn.

The clamping structure on the stationary mouthpiece consists of a stationary half and another half which is pivotable. The pivotable half is installed for that purpose on a lever which is supported rotatably about a predetermined angle and which is operable by means of a pedal switch.

The other design embodiment of the stitching apparatus includes a mouth area which is in parallel alignment with the axis of the apparatus. The movable mouthpiece is supported so as to be movable about an axis which extends normal to the axis of the apparatus so that the movable mouthpiece can be pivoted open by a predetermined angle or it can be pivoted onto the stationary mouthpiece.

The clamping structures are the same as described above. Only the movable half of the clamping structure of the stationary mouthpiece is now not pivoted onto the stationary half but is slidable toward or away therefrom. The drive mechanism therefor is, like above, operated by a pedal switch.

This particular stitching apparatus design is suitable especially also as a grasping instrument. The free ends of the mouthpieces are therefore suitably grooved.

In order to avoid tearing of the tissue or vessels during the stitching procedure utilizing this apparatus, the stitching needle employed is so curved that its axis coincides with the path of movement of the clamping structure at the movable mouthpiece.

The two discs, that is, the two halves of the respective clamping structure, are exchangeable such that halves corresponding to the shapes of the tips of the utilized needles can be inserted. This has the economical advantage that various needle types can be handled by a single stitching apparatus.

This advantage permitting removal and installation of various clamping structures is expandable in such a manner that the stitching apparatus can be utilized not only for stitching but also for stapling vessel or tissue parts if the clamping structure can be replaced by a stapling support structure and the respective boss structure.

BRIEF DESCRIPTION OF THE DRAWINGS

Below, the invention is described in greater detail on the basis of embodiments shown in the drawings, wherein.

DESCRIPTION OF THE PREFERRED EMBODIMENT

Figure 1:
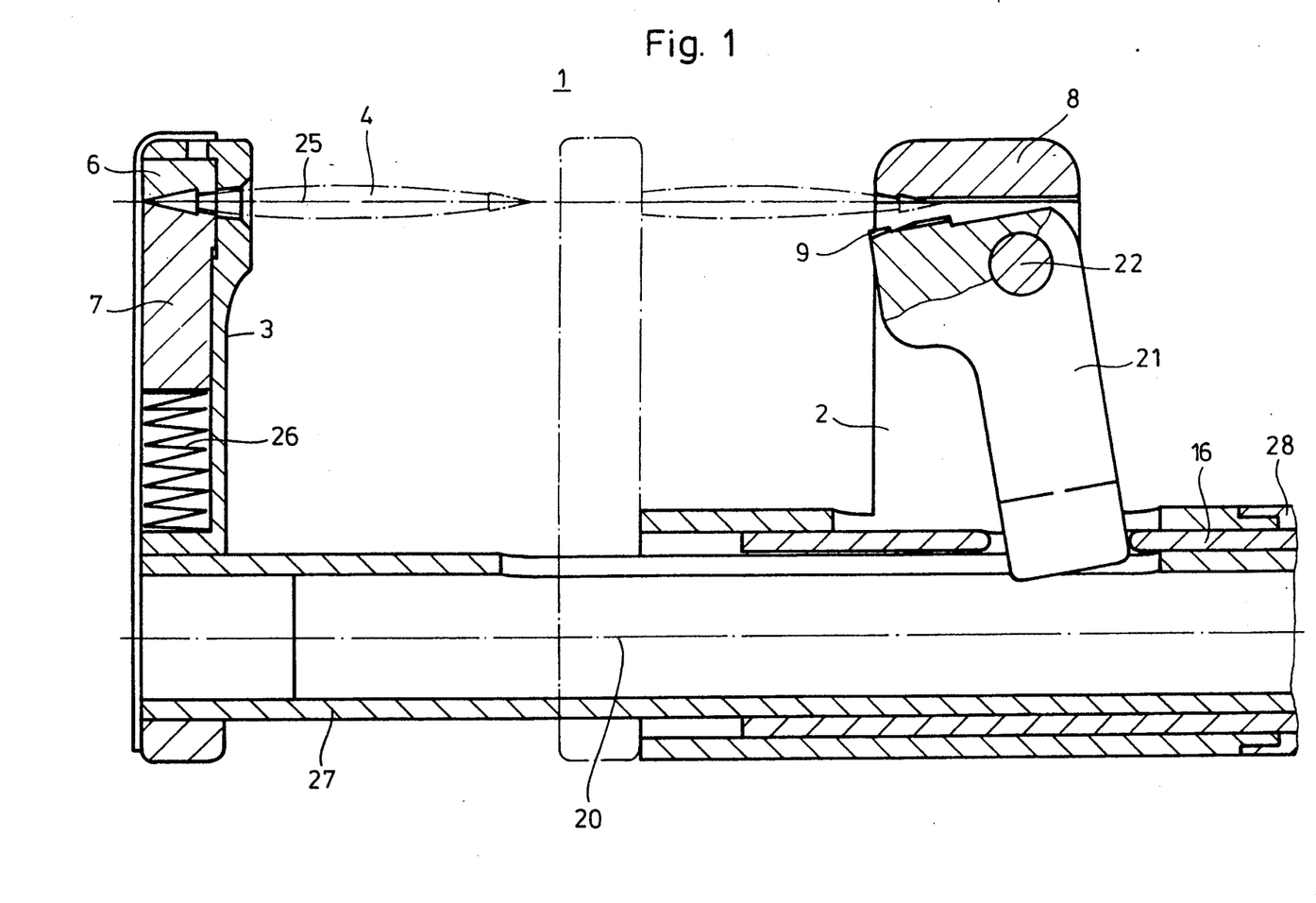
FIG. 1 shows the stitching apparatus with a mouth area arranged at the side thereof.

FIG. 1 is a side view of the stitching head 1 of the surgical stitching apparatus. It comprises the two mouthpieces 2, 3 which extend in the same direction normal to the axis 20 of the stitching apparatus.

Figure 5:
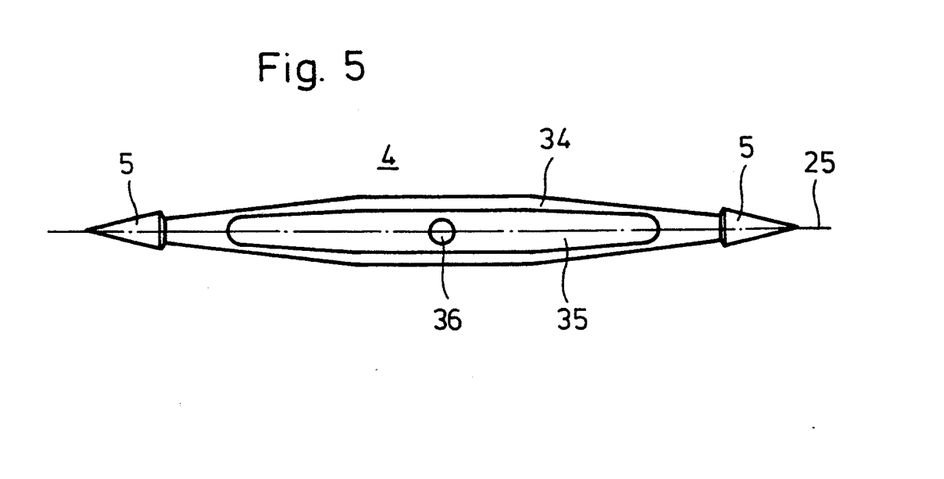
FIG. 5 shows a stitching needle for the apparatus of FIG. 1.

At its free end the mouthpiece 3 includes an insert for the clamping structure 6, 7 which is provided with an arrow-shaped cavity. The axis 25 of this clamping structure 6, 7 extends parallel to the axis 20 of the stitching apparatus. The clamping structure 6, 7 can be assembled on, or disassembled from, the mouthpiece 3 from the free head side thereof. It consists of two halves 6, 7. The one half 6 is stationary. The other movable half 7 is forced toward the one half by means of a spring 26 with predetermined spring constant so that, in engagement with one another, they define therebetween the negative form of the needle tip 5 (FIG. 5). The needle is therefore engaged in form and force-locking relationship. In this manner axial and radial forces are applied to a needle tip engaged therein over its hole circumference. However, with the application of a certain axial force, the needle can be pulled out of the clamping structure. The mouthpiece 3 is firmly connected to the coaxial tube 27 and is movable back and forth therewith in axial direction. This is achieved by operating the movable part of the operating handle structure (see FIG. 3).

Opposite the movable clamping structure the other stationary clamping structure 8, 9 for the needle 4 is disposed on the stationary mouthpiece 2. This clamping structure 8, 9 can be closed and opened by means of the pivotally supported lever 21. The lever 21 is pivotal about the pivot axis 22 whereby the movable half 9 of the clamping structure 8, 9 is pressed onto the stationary half 8 or is pivoted away therefrom. The lever 21 is operated by means of the tube 16 which again is operated by the drive structure 13, 14 15 on the operating handle structure 10.

This arrangement easily prevents transfer of the stitching needle 4 from one clamping structure 6, 7 to the other 8, 9 or even simultaneous clamping of both needle tips 5. Form and force-locking engagement in both clamping structures 6, 7; 8, 9 retains the needle in every case in the predetermined position.

Figure 2:
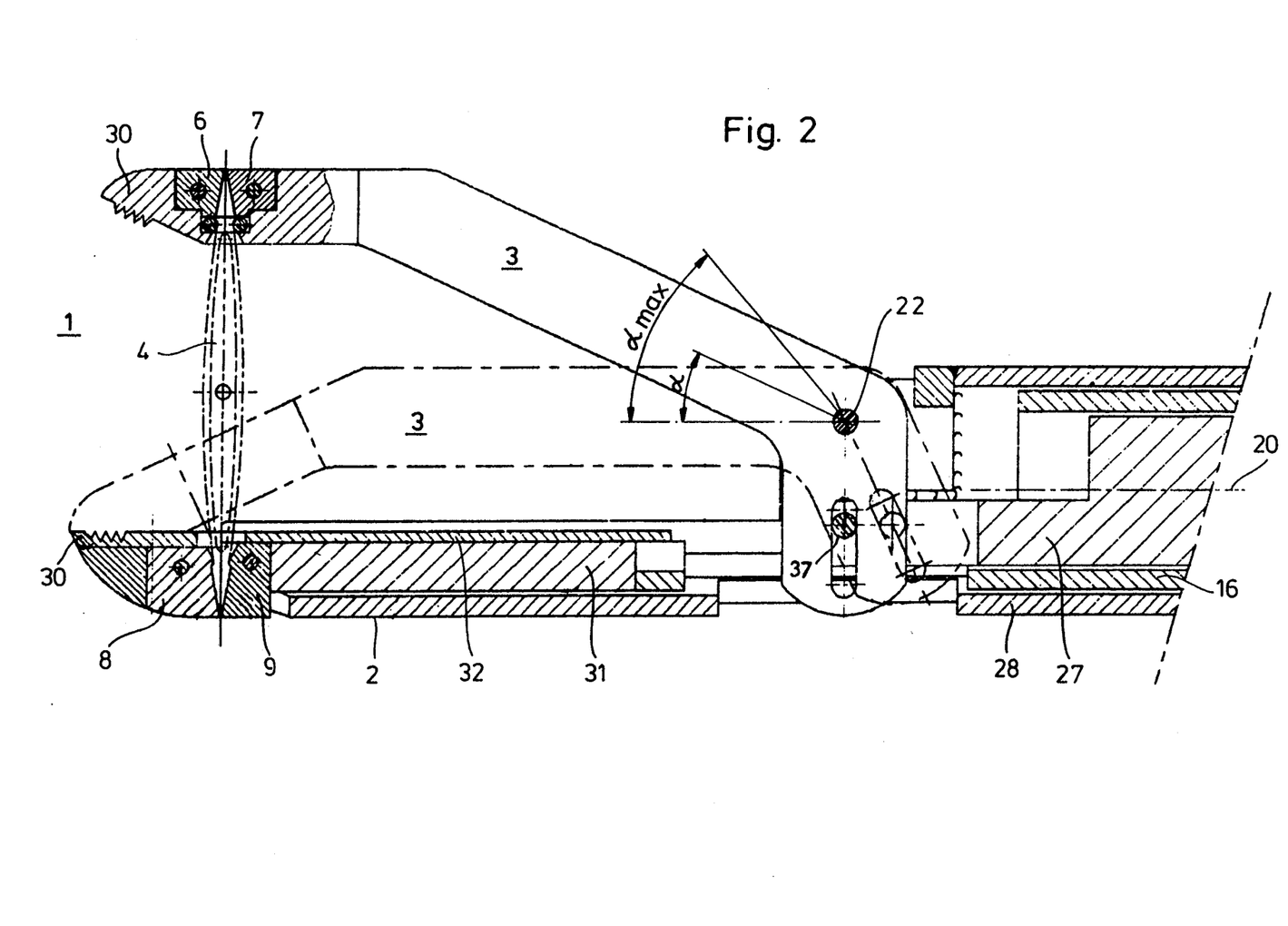
FIG. 2 shows the stitching apparatus with the mouth area arranged in front.
Figure 3:
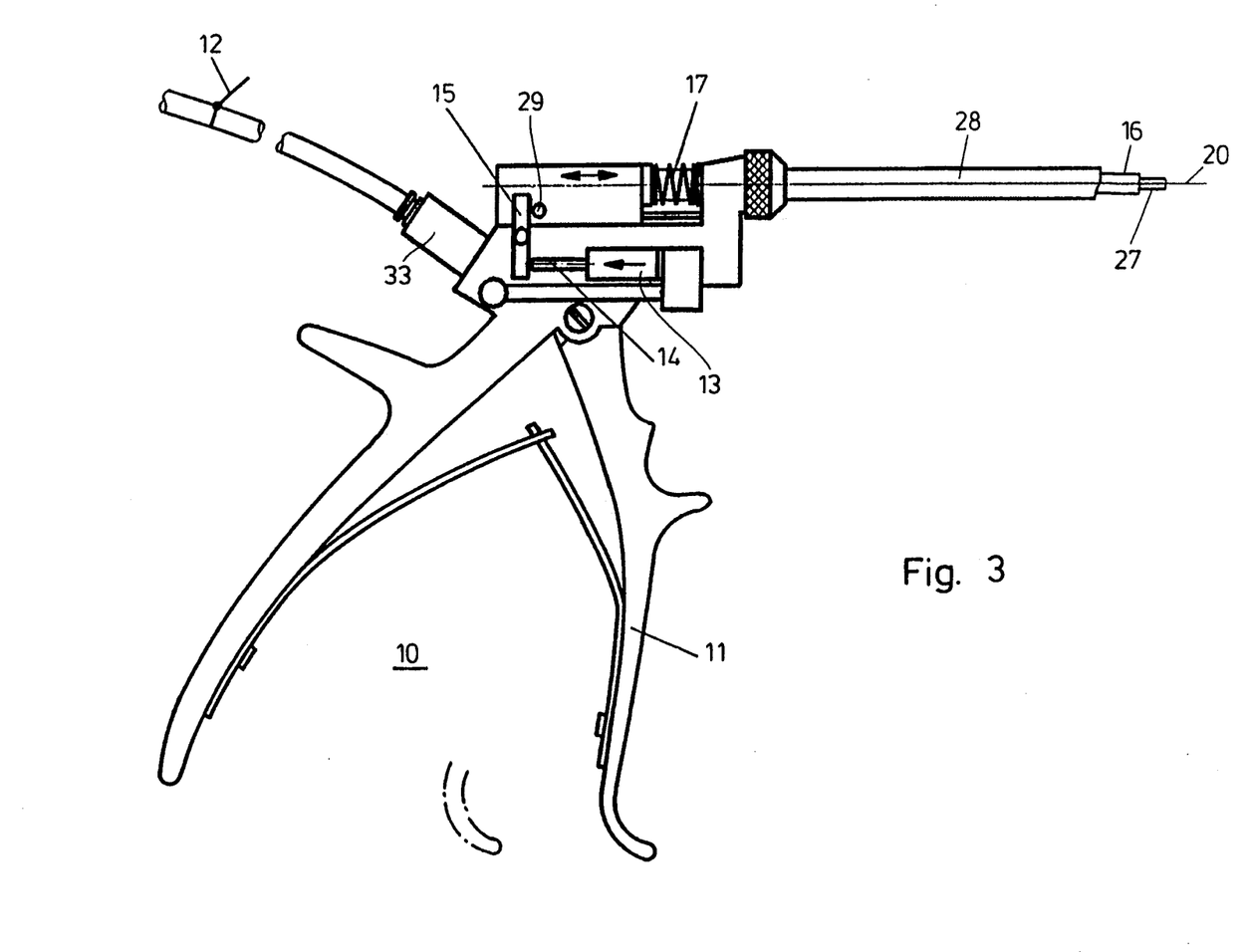
FIG. 3 shows the operating handle structure for operating the stitching apparatus.

The stitching head 1 of FIG. 1 is, by design, oriented differently. The opening of the mouthpieces 2, 3 is toward the front as seen from the instrument axis 20. The stationary mouthpiece 2 is disposed parallel to, that is, adjacent to, the instrument axis 20. The other, movable mouthpiece 3 can be pivoted open and closed and is supported on the pivot axis 22. It is movable about an angle $\alpha$ predetermined by design (FIG. 2). For operation a coaxial tube 16 disposed within the instrument tube 28 and, at its end, coupled to the mouthpiece 3 by means of bolts 37 is to be moved back and forth by way of operating handle 11 (FIG. 3). If no needle 4 is mounted in one of the clamping structure 6, 7; 8, 9 the movable mouthpiece can be closed such that the two ribbed surfaces 30 firmly engage one another. The stitching head 1 of the stitching apparatus is therefore also usable as a clasping apparatus. The mouthpiece 3 is shown in this position in dash-dotted outline.

At the distal end of the two mouthpieces 2, 3 directly behind the ribbed surfaces 30, there are provided easily releasable clamping structures 6, 7; 8, 9. Both clamping structures 6, 7; 8, 9 define cavities corresponding to the negative shape of the needle tip 5 with a circular, or triangular or multiangular cross-section. The last mentioned are used to prevent axial rotation of a needle engaged in the clamping structure.

The clamping structure 8, 9 in the stationary mouthpiece 2 comprises, as shown in FIG. 2, two halves 8, 9. The one half 8 is firmly mounted on the mouthpiece 2. The other half 9 is mounted to the front end of the tube 16 adjacent the sliding mechanism 31 and can be moved therewith back and forth so that the clamping structure 8, 9 can be opened and closed. The needle 4 can therefore be engaged in a form- and force-locking manner. Operation of the mechanism is achieved via the operating handle structure 10 in the manner explained in connection with FIG. 1.

It also has been found suitable to cover the sliding mechanism 31 between the movable half 9 and the end of the operating tube 27 adjacent the space between the two mouthpieces with a metal sheet 32.

The clamping structure 6, 7 on the movable mouthpiece 3 is identical in structure with the one of the corresponding mouthpiece of FIG. 1 and consequently function and action are the same.

The needle shown in dashed lines is straight in this arrangement. This poses no problem from a surgical point of view for small maximum opening angles α max. For larger opening angles α max which may be formed between the two mouthpieces, it is advantageous if the needle 4 is curved in order to avoid tearing of the tissue or vessels (see below the description of FIG. 4).

The stitching heads as described in FIGS. 1 and 2 can be operated by means of operating handle structure 10. Operating movements generated in the operating handle structure are transmitted via a tubular drive through a trocar-like structure to the stitching head 1 and converted to stitch and also transfer movements.

It is advantageous for the surgeon if the actual stitching can be performed with one hand while the other hand can be used for control movements if this is necessary. Consequently the needle in the switch-over procedure should be released without confusion during switchover. This is possible with the foot-operated pneumatic mechanical drive at the operating handle structure.

For this purpose a miniature pneumatic cylinder 13 is installed on the upper part of the operating handle structure 10 which includes a piston rod 14 arranged parallel to the axis 20 of the apparatus and movable by means of pressurized air supplied to the cylinder. The piston rod 14 engages a lever 15 which is pivotally supported on the upper part of the operating handle structure and which with its lever part engages a pin 29 for moving the tube 16 forwardly in opposite direction. The clamping structure 8, 9 of the stationary mouthpiece 2 of FIG. 1 is closed thereby, so that form and force-locking engagement with the needle 4 is achieved. This condition is maintained as long as pressurized air is applied to the piston in the cylinder 13. This condition is quite helpful under certain circumferences. Because of it, the surgeon can slide tissue onto the needle 4 which is then clamped to the stationary mouthpiece 2. In order to be able to maintain this condition the pressurized air supply line extends through a lockable pedal switch 12 which can be operated by the foot of the surgeon or an assistant standing directly beside the surgeon. From the pedal switch 12 the pressurized air pipe extends to the connecting nozzle 33 on the upper part of the operating handle structure 10 from where a pressure pipe extends to the pneumatic cylinder 13.

If the pedal switch is pushed down beyond its locking position it is released and it returns whereby admission of pressurized air is blocked. The pressurized air in the pneumatic cylinder 13 is then released. Subsequently the tube 16 is automatically pulled back by the return spring 17 surrounding the tube 16 and held at its near end adjacent the operating handle structure 10 whereby the needle tip 5 engaged by the stationary mouthpiece 3 is released.

The pivot point of the lever 15 between the axis of the piston rod and the instrument axis 20, that is, the effective lever arm between the piston rod and the lever pivot point and also between the lever pivot point and the pin 29, are adjustable. This permits adjustment of the force applied to the tube 16 such that it is limited and application of unnecessary forces to the head of the stitching apparatus are avoided.

Figure 4:
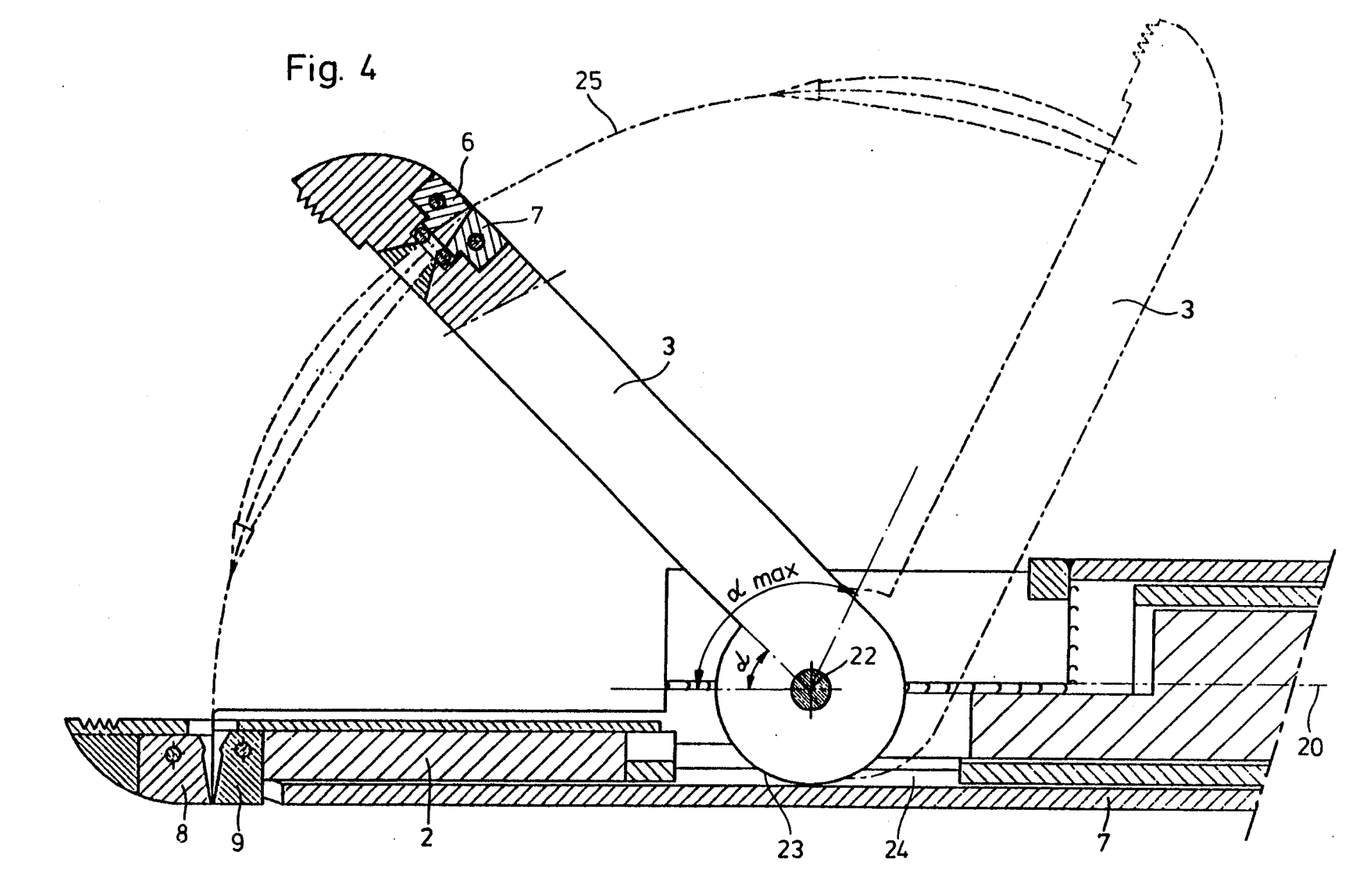
FIG. 4 shows a mouthpiece of a stitching apparatus according to FIG. 2, operated by means of a rack and pinion drive.

For a larger opening angle α max FIG. 4 shows once more the embodiment of FIG. 2.

The pivotally mounted end of the movable mouthpiece 3 is provided with gear ring 23 which is concentric with the pivot axis 22 and which is engaged by a longitudinally movable gear rack 24 and which, depending on its direction of movement and the extent of movement, pivots the movable mouthpiece within the maximum opening angle α max to a more or less open or closed position. Since the angle α max may, by design, be quite large, such a stitching apparatus requires the use of a curved stitching needle 4. If the needle 4 has a curvature corresponding to the path of movement 25 of the clamping structure 6, 7, it merely pierces the tissue or a vessel wall and will not cause any additional tearing.

Figure 6:
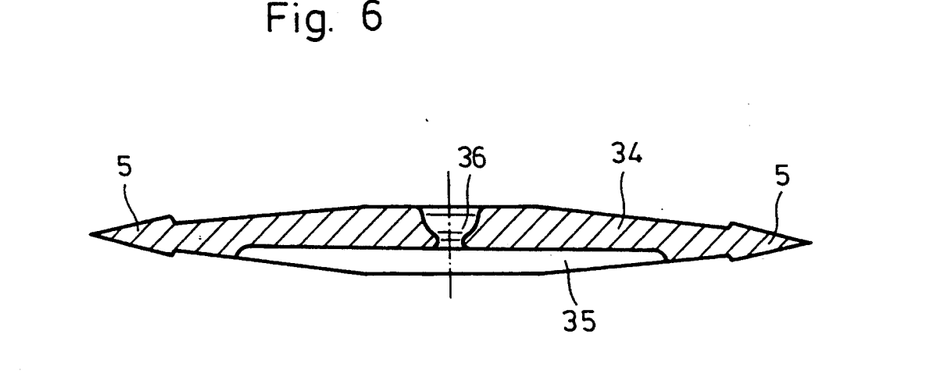
FIG. 6 is a longitudinal cross-sectional view of the stitching needle.
Figure 7:
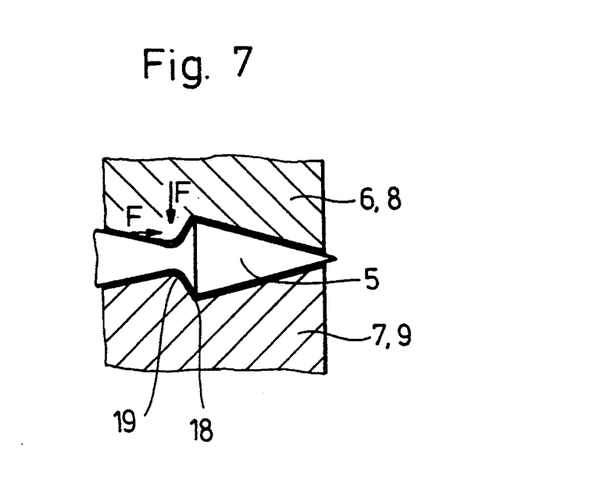
FIG. 7 shows a stitching needle engaged by the clamping structure.

In FIGS. 5, 6 and 7 the needle 4 indicated in FIGS. 1 and 2 by dashed lines is shown in top view, in a longitudinal cross-section and as a partial view showing the needle tip.

The stitching needle 4 itself is shuttle-like and symmetrical along its longitudinal axis 25. At both ends, it has equally shaped tips 5 which extend the needle body 34 via a bulge. The needle body 34 itself includes a longitudinal cavity 35 with a transverse bore at the bottom forming the needle eye 36. There particularly, all edges are rounded. The stitching thread ends at this point and is attached there by a knot without projecting outwardly. Furthermore, during the stitching procedure it is received in the longitudinal cavity 35 so that tearing of the tissue during piercing is prevented.

FIG. 7 highlights the engagement of the needle tip 5 by the two halves 6, 8; 7, 9 of the clamping structure. Because of the truncated cone-like transition between the bulge 18 and the needle body no excessive forces are in effect so that, on one hand, a clearly defined orientation of the needle 4 is obtained by the form- and force-locking engagement of the needle but, on the other hand, insertion or removal of the needle 4 can be achieved by application of a predetermined force. The force directions applied around the reduced shank portion 19 of the engaged needle 4 are clearly indicated by the perpendicularly extending arrows F.

Below, a stitching procedure will be described wherein also the change-over procedure for the needle is explained:

First, the stitching needle 4 which is attached to one end of the stitching thread is placed longitudinally between the closed or almost closed mouthpieces 2, 3 and eventually is engaged at one of its tips between the two ribbed surfaces 30. Then the stitching instrument is inserted through the instrument channel to the stitching location. During this process the stitching thread is pulled along through the tubes 16, 27. At the stitching location the movable mouthpiece 3 is opened and the stitching needle 4 is inserted by means of a grasping instrument extending through another instrument channel into one of the clamping structures, preferably into the stationary mouthpiece 2, since this can be opened and closed from without. At this point, a first stitch can be made through the tissue to be sutured. Then the movable mouthpiece 3 is pivoted in the direction toward the mouthpiece 2 until the free needle tip 5 is finally engaged in the clamping structure 6, 7. Then the needle 4 is released from the clamping structure 8, 9 by operation of the pedal switch 12 and is pulled, together with the stitching thread, fully through the tissue. The stitching procedure can be continued by appropriate stitching and needle switch-over. However, if necessary, a knot can be tied after each stitching step and pulling through of the thread whereupon the knot on the stitching thread is pulled tight eventually by means of an additional instrument.

The dimensions of the stitching head of a prototype model of the inventive apparatus described herein were very small as desired. The length of the stitching head, for example, was 17 mm. The length of the movable mouthpiece was 12 mm. Both mouthpieces had a thickness of only about 1.5 mm. The stitching head was movable through an instrument channel with an inner diameter of 5 mm and could be operated successfully.

The expected advantage of a simple operating procedure at the operating handle structure and the needle disengagement during the stitching and needle transfer process was achieved.

What is claimed is:

1. A surgical stitching apparatus for endoscopically forming surgical stitches in tissues or vessels by means of a stitching needle, said apparatus comprising a drive mechanism including concentric tubes, a stitching head mounted on a distal end of said concentric tubes, an operating handle structure mounted on a proximal end of said drive mechanism and having means connected to said concentric tubes for movement thereof for operation of the stitching head at the distal end of said drive mechanism, said stitching head having a stationary and a movable mouthpiece arranged so as to be movable relative to one another along a predetermined path, each having a clamping structure, the clamping structure on the movable mouthpiece including a spring mechanism for biasing the clamping structure thereon into a closed position and the clamping structure on said stationary mouthpiece being operable by said operating handle structure via one of said concentric tubes, said stitching needle having at each end a tip with a bulge and a reduced shank portion and said clamping structures having cavities formed therebetween for receiving the needle tips in a form- and force-locking manner, said needle being formed such that its longitudinal axis coincides with the path of relative movement of said clamping structures, said movable mouthpiece being operatively connected via another of said concentric tubes to a handle on said operating handle structure for hand control of the relative movement of said mouthpieces, and the clamping structure on said stationary mouthpiece being operable by means of a pedal switch operated drive mechanism disposed on said operating handle structure and connected to said one concentric tube, said drive mechanism comprising a miniature pneumatic cylinder mounted on said operating handle structure and operatively connected to said one concentric tube for operation of the clamping structure on said stationary mouthpiece.

2. A stitching apparatus according to claim 1, wherein said miniature pneumatic cylinder is disposed parallel to the axis of said concentric tubes and spaced therefrom and has a piston with piston rod extending from said cylinder and being connected to said one concentric tube by means of a switch lever pivotally supported between said pneumatic cylinder and said concentric tubes so as to transfer movement from said piston rod to said one concentric tube with a predetermined force depending on the effective lengths of the arms of the switch lever.

3. A stitching apparatus according to claim 2, wherein said miniature pneumatic cylinder and said switch lever are so arranged that pressurized air admitted to said cylinder biases said one concentric tube forwardly for closing the clamping means and holding it closed and wherein return spring means are connected to said one concentric tube and said clamping structure for pulling back said one concentric tube and opening said clamping means when the air pressure in said miniature cylinder is released.

4. A stitching apparatus according to claim 1, wherein said cavities formed between said clamping structures define negative shapes of the needle tips and the areas defining said bulge and reduced shank portions are rounded and provided with smooth truncated cone transitions which facilitate insertion and removal of the needle tips with predetermined force.

5. A stitching apparatus according to claim 1, wherein said handle on said operating handle structure is position lockable so as to permit maintaining said mouthpieces in predetermined relative positions.

6. A stitching apparatus according to claim 1, wherein said mouthpieces extend perpendicularly from the longitudinal axis of said stitching head, a needle held between said mouthpieces extends parallel to said longitudinal axis and said clamping structure on the stationary mouthpiece comprises a stationary half and a movable half pivotally supported on said stationary mouthpiece and engageable with said stationary half by a lever extending from said movable half and engaged by said one concentric tube.

7. A stitching apparatus according to claim 1, wherein said stationary mouthpiece is disposed along an extension of the axis of said apparatus and said movable mouthpiece is supported pivotally about a pivot axis extending in a plane perpendicularly thereto and said other concentric tube is in engagement with said movable mouthpiece for pivoting said movable mouthpiece relative to the stationary mouthpiece within a predetermined angular range between a closed and open position.

8. A stitching apparatus according to claim 7, wherein said movable mouthpiece is provided at its pivot axis with a concentric gear ring which is engaged by a gear rack connected to said other concentric tube and axially movable therewith for pivoting said movable mouthpiece.

9. A stitching apparatus according to claim 7, wherein said needle is curved so as to correspond in shape to the path of movement of the clamping structure on the movable mouthpiece.

10. A stitching apparatus according to claim 1, wherein said clamping structures comprise exchangeable inserts for use with different needle tips.

11. A stitching apparatus according to claim 1, wherein said clamping structures comprise exchangeable inserts for receiving other types of suturing devices.

12. A stitching apparatus according to claim 1, wherein said mouthpieces have ribbed end portions for grasping tissue when no needle is disposed between the mouthpieces.

* * * * *